United States Patent [19]

Armstrong et al.

[11] Patent Number: 5,543,418
[45] Date of Patent: Aug. 6, 1996

[54] INNOVATIVE TECHNIQUE FOR IMMUNOSUPPRESION INVOLVING ADMINISTRATION OF RAPAMYCIN LOADED FORMED BLOOD ELEMENTS

[75] Inventors: Jay J. Armstrong, Bensalem, Pa.; Surendra N. Sehgal, Princeton, N.J.

[73] Assignee: American Home Products Corporation, Madison, N.J.

[21] Appl. No.: 423,133

[22] Filed: Apr. 18, 1995

Related U.S. Application Data

[62] Division of Ser. No. 998,065, Dec. 22, 1992, Pat. No. 5,482,945.

[51] Int. Cl.$^6$ .................................................. A61K 31/44
[52] U.S. Cl. .................................................. 514/291
[58] Field of Search .................................................. 514/291

[56] References Cited

U.S. PATENT DOCUMENTS

| | | | |
|---|---|---|---|
| 3,929,992 | 12/1975 | Sehgal | 424/122 |
| 4,401,653 | 8/1983 | Eng | 424/114 |
| 4,885,171 | 12/1989 | Surenda | 424/122 |
| 4,887,995 | 12/1989 | Abraham | 604/4 |
| 5,078,999 | 1/1992 | Warner | 424/122 |
| 5,100,899 | 3/1992 | Caine | 514/291 |

OTHER PUBLICATIONS

Abraham et al., Transplantation 52(1), 101–105 (1991).
Bowers et al., Transplantation 51(4) 847–50 (1991).
Lorenz et al., Agents and Actions 12(1/2), 64–80 (1982).
Cybulska et al., Japanese J. Pharmacology 55 (Supp. I), 202P, 0–412 (1991).
Kitao and Hattori, Cancer Research 40, 1351–1353 (1980).
Stepkowski and Kahan, Transplantation Proceedings 23(6), 3262–3264 (1991).
Chen et al., Transplantation Proceedings 23(4), 2239–2246 (1991).
Kay et al., Transplantation Proceedings, 23(6), 2760–2762 (1991).
Stepkowski et al., Transplantation 51(1), 22–26 (1991).
Martel et al., Can J. Physiol. Pharmacol. 33, 48–51 (1977).
Staruch et al., FASEB Journal 3(3), 3411 (1989).
DuMont et al., FASEB Journal 3(4) 5256 (1989).
Sehgal et al., J. Antibiotics 28(10), 727–32 (1975).
Baker et al., J. Antibiotics 31(6), 539–545 (1978).
Verzina et al., J. Antibiotics 28(10), 721–726 (1975).
Hoefnagels et al., The Lancet 901 (1988).
Dye and Walkins, British Medical Journal 1353, (1980).
Gruber et al., Pharmaceutical Research 6(7), 601–607 (1989).
Howrie et al., Drug Intel. Clin. Pharm. 19 425–427 (1985).
O'Leary et al., Surg. Gyn. Ob. 154, 681–688 (1982).
Zincke and Woods, Surg. Gyn. Ob., 145, 183–188 (1977).
Alejandro et al., Diabetes 36, 269–273 (1987).
Bowen et al., Diabetes 29, (Supp. 1), 98–104 (1980).
Lagudzinski and Gorski, Folia Biologica (Praha)37, 21–26 (1991).
MacLeod, Immunology Letters 29, 123–125 (1991).
Gregory et al., J. Heart Lung Transplantation 11(1), pt. 2, 197 (1992).
Stepkowski et al., Transplantation Proceedings 23(1), 507–508 (1991).
Lemaire and Tillement, J. Pharm. Pharmacol. 34, 715–718 (1982).
Brom et al., Kidney International 21, 323–329 (1982).

*Primary Examiner*—Jerome D. Goldberg
*Attorney, Agent, or Firm*—R. F. Boswell, Jr.

[57] ABSTRACT

This invention relates to a technique for treating a mammal with rapamycin which comprises removal of blood from the patient, treatment of the formed blood elements with rapamycin which binds rapidly and reversibly with erythrocytes, and returning the treated blood cells to the circulatory system of the patient for the treatment of any of the diseases, syndromes, conditions, or immune responses which respond to treatment with rapamycin. Alternatively, blood to be treated with rapamycin can be obtained from a hematologically compatible donor mammal.

1 Claim, No Drawings

INNOVATIVE TECHNIQUE FOR IMMUNOSUPPRESION INVOLVING ADMINISTRATION OF RAPAMYCIN LOADED FORMED BLOOD ELEMENTS

This is a division of application Ser. No. 07/998,065, filed Dec. 22, 1992, now U.S. Pat. No. 5,482,945.

FIELD OF INVENTION

This invention relates to an innovative technique for administering rapamycin intravenously or intraarterially wherein mammalian formed blood elements are loaded with rapamycin extracorporeally by incubating with a solution of rapamycin and the rapamycin-loaded formed blood elements are then administered to the circulatory system of a mammal for suppression of immune responses or treatment of diseases which respond to treatment with rapamycin. Rapamycin has been shown to have immunosuppressive and antiproliferative properties, to be useful in inhibiting transplant and/or graft rejection, in the treatment of certain cancers or tumors, in the treatment of autoimmune diseases such as systemic lupus erythematosus and respiratory inflammatory disease, and in treating smooth muscle cell proliferation and intimal thickening following vascular injury [Morris, R. J. Heart Lung Transplant 11 (pt. 2) 197 (1992)].

BACKGROUND OF THE INVENTION

Extracorporeal treatment of blood involves treatment of the whole blood or components thereof to remove or add a component or alter a blood component, and returning the treated blood to the mammal to obtain a desired effect. Sickle cell anemia can be treated by extracorporeal treatment of blood with ethacrynic acid, cyanate, or nitrogen mustard. Cholesterol levels can be lowered by extracorporeal treatment of blood with heparin-agarose beads to which low density plasma lipoproteins selectively bind. Beads of cross-linked agarose containing Fuller's earth or zirconium oxide powders have been used extracorporeally in blood detoxification to remove Paraquat or inorganic phosphates. Toxic effects of cisplatin used in treating human malignant glioma have been minimized by infusing cisplatin into the internal carotid artery and extracorporeally removing most of the cisplatin from the jugular venous flow by dialysis thereby minimizing the amount of cisplatin that enters the body below the neck. Other extracorporeal blood treatment methods include removal of T-cells, photopheresis where blood is exposed to ultraviolet light, removal of antibodies and immune complexes in the treatment of allergies, immune disorders, and systemic lupus erythematosus, and ion-exchange resin treatment of blood to improve serum protein binding of acidic drugs in patients having uremia.

The immunosuppressant macrolide FK-506 has been shown to be absorbed and retained by peripheral blood mononuclear cells and erythrocytes and to bind reversibly with a FK-506 binding protein (FKBP) in the erythrocytes. FK-506 inhibits the activation of T-lymphocytes and is available to the lymphocytes by dissociation from FKBP.

Daunomycin, an antileukemic drug, will not bind to red blood cells. If the red blood cells are first treated with Amphotericin B, a polyene macrolide that binds to sterols and perforates cell membranes, then the treated red blood cells will bind daunomycin. Mice bearing L1210 leukemic cells had a prolonged survival time when treated with erythrocytes with entrapped daunomycin. Other polyene macrolides, such as vacidin A and related compounds, bind with red blood cells and cause hemolysis to occur. The polyene macrolide antibiotic, faeriefungin, has erythrocyte toxicity similar to Amphotericin B.

DESCRIPTION OF THE INVENTION

Rapamycin, a triene macrolide, has been found to bind reversibly with the binding protein FKBP in formed blood elements (erythrocytes) but does not cause hemolysis like the aforementioned polyene macrolides.

In human blood, erythrocytes comprise about 85 to 90 percent of the formed blood elements (microscopically visible). Human whole blood is comprised of about 46% formed blood elements and 54% plasma. Equilibrium of rapamycin between the rapamycin-loaded formed blood elements (FBE) and the plasma is quickly established and is seen to be species dependent. In rat blood containing rapamycin at a concentration of 38 ng/ml, the whole blood and FBE to plasma ratios were 1.3 and 1.7 respectively and at a concentration of 200 ng/ml the ratios were 0.8 and 0.5 respectively.

In human blood at rapamycin concentrations between 76 and 189 ng/ml, the whole blood and FBE to plasma ratios after 30 minutes incubation at 37° C. were 12±2 and 23.7±3.9 respectively. Similarly, at a concentration of 482 ng/ml, the ratios were 1.1 and 1.3 respectively. The ratios of whole blood to plasma concentrations in monkeys receiving rapamycin was 10±6 and in humans the ratio was 12±2, and indication that a species difference exists between primates and other mammals.

This invention therefore is concerned with a method of treating the diseases, syndromes, and unfavorable immunological responses which respond to treatment with rapamycin wherein the rapamycin is delivered by rapamycin-loaded formed blood elements, said rapamycin-loaded FBE being prepared extracorporeally.

The following United States patents and journal articles describe the immunosuppressant, antiinflammatory, antitumor and antifungal properties of rapamycin and are herein incorporated by reference: U.S. Pat. No. 5,100,899, which discloses inhibition of transplant rejection; U.S. Pat. No. 3,993,749 which discloses antifungal properties, U.S. Pat. No. 4,885,171 which discloses antitumor activity against lymphatic leukemia, colon and mammary cancers, melanocarcinoma and ependymoblastoma; U.S. Pat. No. 4,401,653 which discloses the use of rapamycin in combination with picibanil in the treatment of tumors; U.S. Pat. No. 5,078,999 which discloses a method of treating systemic lupus erythematosus; U.S. Pat. No. 5,080,899 which discloses a method of treating pulmonary inflammation and is thus useful in the symptomatic relief of diseases in which pulmonary inflammation is a component, i.e., asthma, chronic obstructive pulmonary disease, emphysema, bronchitis, acute respiratory distress syndrome, or the like; Dumont et al., FASEB Journal 3(4), 5256 (1989) which discloses that rapamycin potentiates the suppressive activity of Cyclosporin A in T-cell proliferation, IL-2 production and IL-2R expression in mouse T-cells stimulated with ionomycin + PMA; Martel et al., Can. J. Physiol. Pharmacol. 55, 48 (1977) which discloses that rapamycin inhibits the immune response in rats in three experimental models—experimental allergic encephalomyolitis, a model for multiple sclerosis, adjuvant arthritis, a model for rheumatoid arthritis and prevents humoral (IgE-like) antibodies in response to an albumin allergic challenge; He et al., Transplantation Proceedings 24

(3), 1178 (1992) which discloses donor pretreatment with rapamycin intravenously to reduce graft rejection in rats; and R. Morris, J. Heart Lung Transplant 11(pt. 2):197(1992) where treatment with rapamycin inhibits restenosis (smooth muscle cell proliferation and internal thickening following vascular injury) which can occur after coronary angioplasty. Rapamycin is also useful in the treatment of immunoinflammatory diseases such as psoriasis.

An embodiment of the innovative technique of this invention is to remove blood from a mammal to be treated with rapamycin, separate the FBE from the plasma by centrifugation or filtration methods, load the FBE with rapamycin by incubation, and combine the rapamycin loaded FBE with the plasma or a physiological substitute therefor, and return the rapamycin-loaded reconstituted whole blood to the mammal. In a preferred embodiment of this technique, the separated FBE are incubated with a solution of rapamycin and then the solvent is removed by washing the rapamycin-loaded FBE with sterile phosphate buffered saline or naive plasma.

Another embodiment of this invention is to treat FBE from donor blood with rapamycin as above and administer the rapamycin-loaded donor blood to a hematologically-compatible mammal in need thereof.

Still another embodiment of this invention is to treat the blood of a tissue or organ donor mammal according to the method of this invention and thus prime the organ or tissue to be transplanted with rapamycin to inhibit rejection by the host mammal. Parenteral administration of immunosuppressant agents such as cyclosporin A, cyclophosphamide, methylprednisone, FK506, or rapamycin to a tissue or organ donor before transplant has been shown to reduce rejection of the transplanted tissue or organ.

In a standard pharmacological test procedure designed to measure graft rejection prevention with blood that has been loaded with rapamycin extracorporeally, whole blood from a single Lewis rat (5 ml) was obtained through the abdominal aorta. The blood was centrifuged at 830×G (2000 rpm) and the erythrocyte (RBC) fraction was isolated, washed twice with sterile phosphate-buffered saline (PBS) and resuspended in a fresh volume of PBS or naive plasma equivalent to that of the initial plasma fraction. The erythrocyte/PBS mixture was then incubated with rapamycin (1 mg rapamycin in 10 μl absolute ethanol/1 ml RBC/PBS) at 37° C. for 5 minutes and individual aliquots containing $1.8 \times 10^6$ erythrocytes were obtained.

Male Lewis rats (300–350 g) were cannulated with indwelling Wicks catheters in the abdominal aorta, posteriorially to the renal arteries. The cannulas were flushed with sterile physiological saline prior to being closed to insure patency with the circulation. On the day of cannulation, each animal received a Brown Norway (BN) neonatal rat heart section transplanted into tile left ear and $1.8 \times 10^6$ rapamycin-loaded Lewis erythrocytes were administered via the indwelling cannula. The experimental animals were transfused through the cannula with approximately $1.8 \times 10^6$ rapamycin-loaded Lewis erythrocytes on a daily basis for two weeks. Cardiac contractility of the transplanted BN heart sections was maintained for more than 30 days by this method, and both CD4 and CD8 lymphocyte levels, significant in graft rejection, were seen to be substantially reduced. This standard pharmacological test procedure showed that $1.8 \times 10^6$ rapamycin loaded erythrocytes are approximately equivalent to a 225 μg intravenous dose of rapamycin in preventing graft rejection. In the above standard test procedure, grafted cardiac muscle survival times that are comparable to survival times observed in standard intravenous administration of rapamycin in a non-aqueous vehicle composed of 20% dimethylacetamide, 10% Tween 80® and 70% polyethylene glycol 400 as described on page 22 in Transplantation 51 ( 1 ), 22–26 ( 1991 ). Thus, the innovative technique of this invention is shown to provide an effective method of administering rapamycin.

Based on the data obtained above in Lewis rats, the projected dosage range of rapamycin-loaded FBE is from 0.1 μg to 100 mg/kg day. The preferred dosage range is from 0.001–25 mg/kg/day. The more preferred dosage range is from 0.01–5 mg/kg/day. The dosage administered can be varied by varying the amount of rapamycin-loaded blood administered to the mammal or varying the amount of rapamycin loaded into the formed blood elements. Rapamycin loaded blood can be administered as a bolus or over a period of time as necessary.

Coadministration of other immunosuppressant agents such as cyclosporin A, FK-506, cyclophosphamide, prednisone, methylprednisolone, or azathioprine is within the purview of this invention.

The method of this invention is seen to have several advantages over standard intravenous therapy. The invention provides treatment with rapamycin without the use of an unnatural vehicle. Cremophore EL, the commonly used vehicle for intravenous administration of macrocyclic antibiotics, has caused anaphylactic reactions. Rapamycin loaded into the erythrocytes may be more bioavailable, protected from metabolic breakdown, and through sequestering with intact erythrocytes, may form a substantial drug reservoir where gradual release of rapamycin probably impedes lymphocyte activity against tissue grafting.

Based on the structural similarity of rapamycin with FK-506, it is expected that FK-506loaded FBE would also be useful in the technique of this invention.

What is claimed is:

1. A method for inducing suppression of the immune responses of immunoinflammatory diseases which consists of intravenous or intraarterial administration of a therapeutically effective amount of rapamycin-loaded formed blood elements suspended in blood plasma or a physiological substitute thereof wherein the immunoinflammatory disease is psoriasis.

* * * * *